US012582427B2

(12) United States Patent
Crowley

(10) Patent No.: US 12,582,427 B2
(45) Date of Patent: Mar. 24, 2026

(54) LITHOTRIPTOR SPACERS AND METHOD

(71) Applicant: OLYMPUS AMERICA INC., Center Valley, PA (US)

(72) Inventor: Peter J. Crowley, Norfolk, MA (US)

(73) Assignee: Olympus America Inc., Center Valley, PA (US)

( * ) Notice: Subject to any disclaimer, the term of this patent is extended or adjusted under 35 U.S.C. 154(b) by 913 days.

(21) Appl. No.: 17/648,270

(22) Filed: Jan. 18, 2022

(65) Prior Publication Data

US 2022/0226009 A1     Jul. 21, 2022

Related U.S. Application Data

(60) Provisional application No. 63/138,973, filed on Jan. 19, 2021.

(51) Int. Cl.
*A61B 17/225* (2006.01)
*A61B 17/00* (2006.01)

(52) U.S. Cl.
CPC .. *A61B 17/225* (2013.01); *A61B 2017/00862* (2013.01)

(58) Field of Classification Search
CPC ........ A61B 17/22004; A61B 17/22012; A61B 17/2202; A61B 17/225; A61B 17/2251; A61B 17/2258; A61B 17/32002; A61B 17/320068; A61B 2017/00862; A61B 2017/22014; A61B 2017/22015; A61B 2017/22027; A61B 2017/22079; A61B 2017/320032; A61B 2017/32007; A61B 2017/320072; A61B 2017/320078; A61B 2017/32008; A61B 2017/320084; A61B 2217/005; A61B 2217/007; A61F 9/00745
See application file for complete search history.

(56) References Cited

U.S. PATENT DOCUMENTS

| | | | |
|---|---|---|---|
| 5,989,209 A * | 11/1999 | Barrett | A61F 9/00745 606/107 |
| 2010/0025869 A1* | 2/2010 | Suzuishi | B29C 45/0025 425/543 |
| 2013/0253387 A1* | 9/2013 | Bonutti | A61B 17/3203 601/46 |
| 2016/0302816 A1* | 10/2016 | Clayton | G06F 30/23 |
| 2019/0298571 A1* | 10/2019 | McDonell | A61F 9/00745 |

* cited by examiner

*Primary Examiner* — Robert A Lynch
(74) *Attorney, Agent, or Firm* — Schwegman Lundberg & Woessner, P.A.

(57) ABSTRACT

A medical device and associated methods are disclosed. In one example, the medical device includes a lithotriptor. One or more spacers are included that extend from an outside surface of a hollow shaft of the lithotriptor. At least one longitudinal pathway is included through the one or more lateral spacers. In one example, the one or more lateral spacers includes an elastomer material.

7 Claims, 4 Drawing Sheets

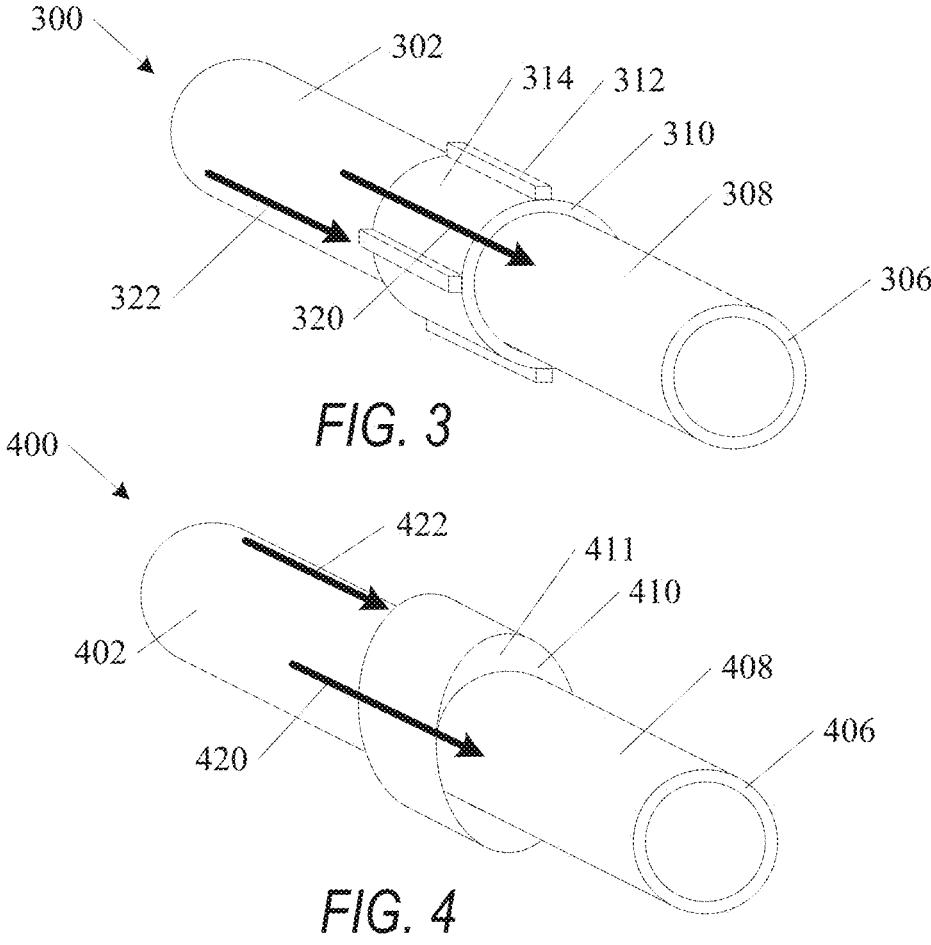
*FIG. 3*
*FIG. 4*
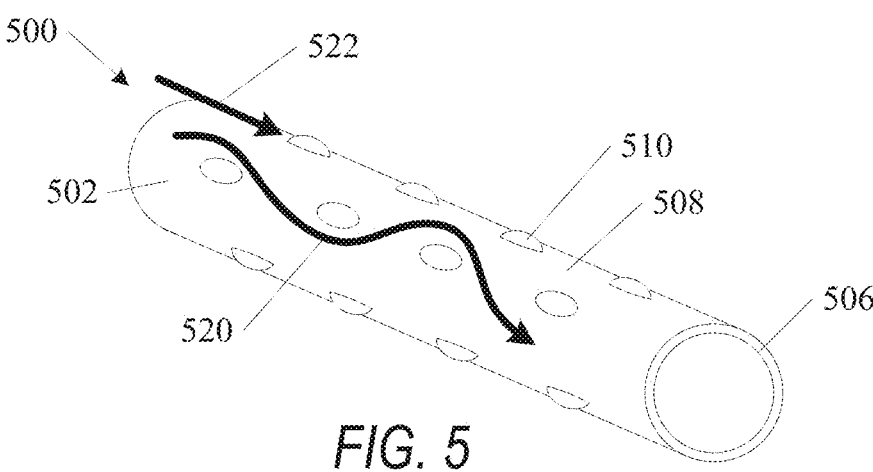
*FIG. 5*

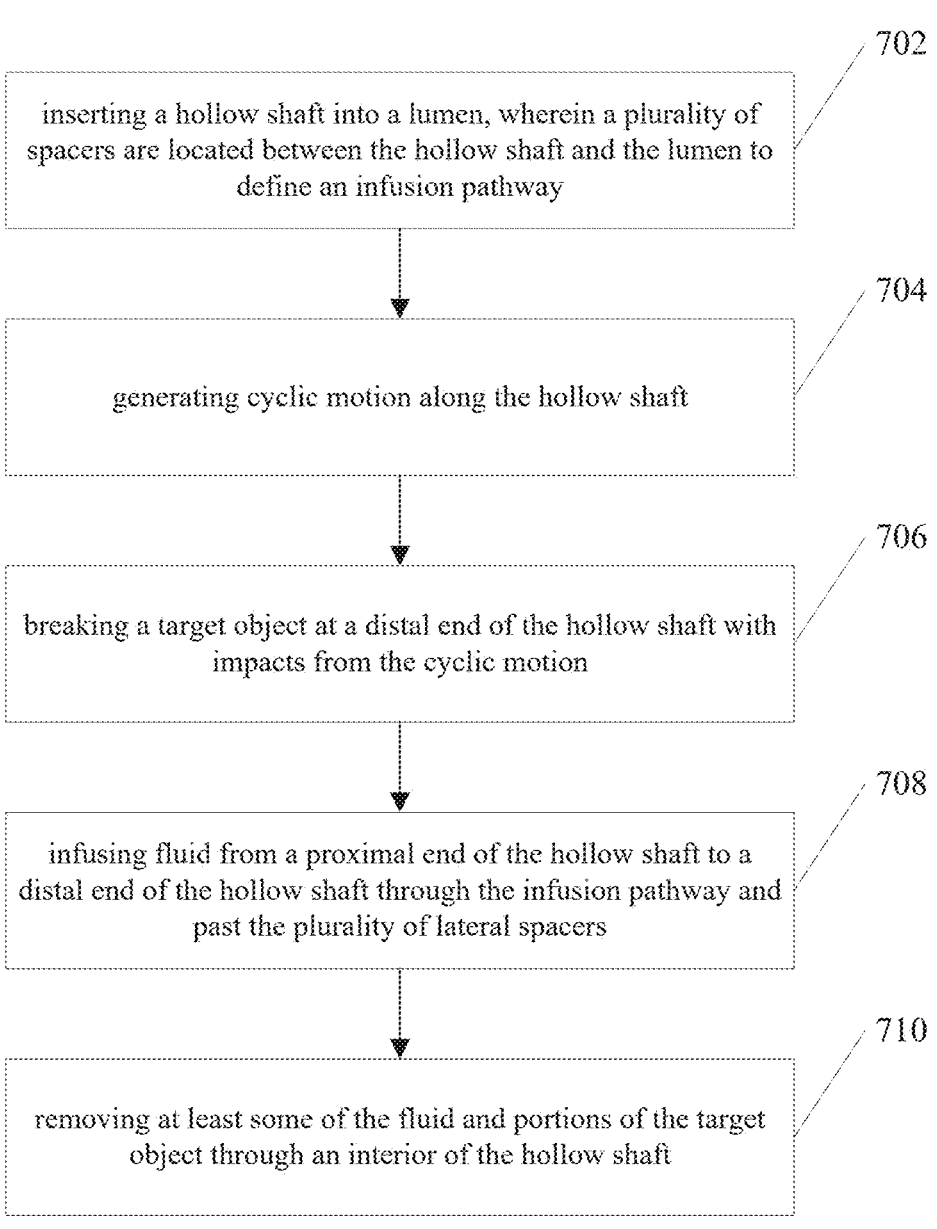

inserting a hollow shaft into a lumen, wherein a plurality of spacers are located between the hollow shaft and the lumen to define an infusion pathway

702 generating cyclic motion along the hollow shaft

704 breaking a target object at a distal end of the hollow shaft with impacts from the cyclic motion

706 infusing fluid from a proximal end of the hollow shaft to a distal end of the hollow shaft through the infusion pathway and past the plurality of lateral spacers

708 removing at least some of the fluid and portions of the target object through an interior of the hollow shaft

LITHOTRIPTOR SPACERS AND METHOD

CLAIM OF PRIORITY

This patent application claims the benefit of priority, under 35 U.S.C. § 119(e), to U.S. Provisional Patent Application Ser. No. 63/138,973, entitled "LITHOTRIPTOR SPACERS AND METHOD," filed on Jan. 19, 2021, which is hereby incorporated by reference herein in its entirety.

TECHNICAL FIELD

Embodiments described herein generally relate to medical devices. A specific example of a medical device includes lithotriptors.

BACKGROUND

Lithotriptors are used to break up and remove unwanted objects from locations within a subject. For example, kidney stones are impacted with a vibrating probed and broken up pieces are removed. The vibrational energy may cause unwanted wear on components due to friction or other contact between components. Improved lithotriptors and methods are desired.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3 shows an end view of a portion of a lithotriptor in accordance with some example embodiments.

FIG. 4 shows an end view of a portion of a lithotriptor in accordance with some example embodiments.

FIG. 5 shows an end view of a portion of a lithotriptor in accordance with some example embodiments.

FIG. 7 shows a flow diagram of a method of using a lithotriptor in accordance with some example embodiments.

DESCRIPTION OF EMBODIMENTS

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

Figure 1:
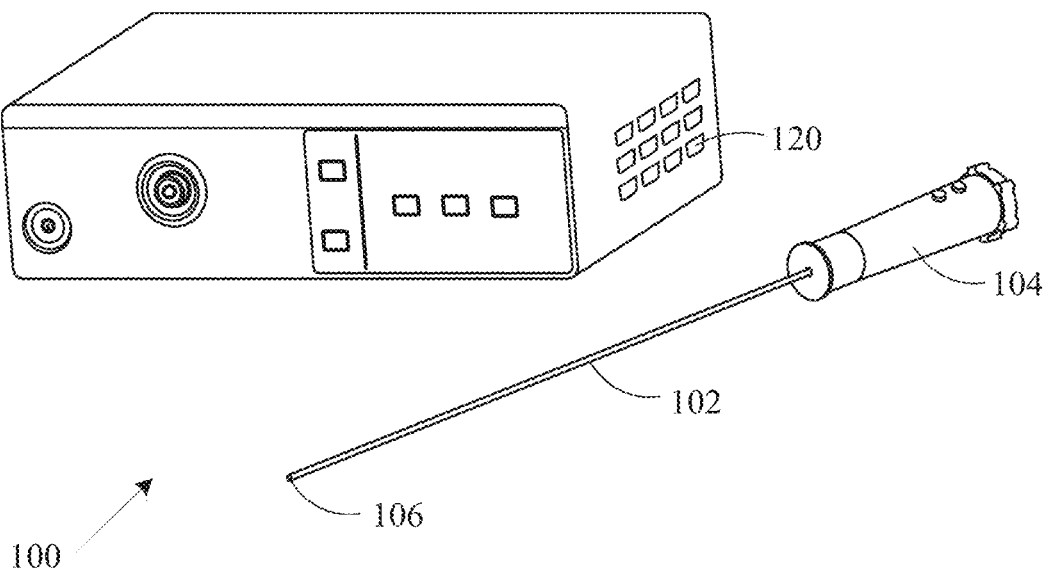
FIG. 1 shows a lithotriptor in accordance with some example embodiments.

FIG. 1 shows a lithotriptor 100 according to one example. In FIG. 1, a hollow shaft 102 extends from a handpiece 104. A controller 120 is used in conjunction with the shaft 102 and handpiece 104 through connecting lines not shown. In one example, the handpiece 104 includes a transducer that is in communication with the controller, for example, through connecting lines. The transducer is configured to receive signals from the controller 120 and generate cyclic motion along the hollow shaft 102. Examples of signals include, but are not limited to sine wave, square wave, combinations of waves, or other electronic signals. In one example, frequencies and amplitudes of signals are varied to provide varying cyclic motion in a distal end 106 of the hollow shaft 102.

In one example procedure, the hollow shaft 102 is inserted into a lumen that leads to a target location, such as a location to break up a stone. The cyclic motion of the hollow shaft 102 and distal end 106 is used to impact and break up the stone. Factors such as friction and vibration between the hollow shaft 102 and the lumen may yield undesirable loss of performance and/or undesirable wear on either the hollow shaft 102 or the lumen.

Although a hollow shaft 102 is described, the invention is not so limited. In selected examples, a solid shaft may be used in place of the hollow shaft 102. In such an example with a solid shaft, broken up fragments of a stone may be removed through suction along one or more longitudinal pathways as described in examples below. Although the longitudinal pathway shaft 102 and/or a solid shaft are shown in various examples with a round cross section geometry the invention is not so limited. Other cross section geometries, such as square, oval, etc. may also be used. Lateral spacers as described in examples below may be attached to a solid shaft example, similar to the hollow shaft examples described.

Figure 2:
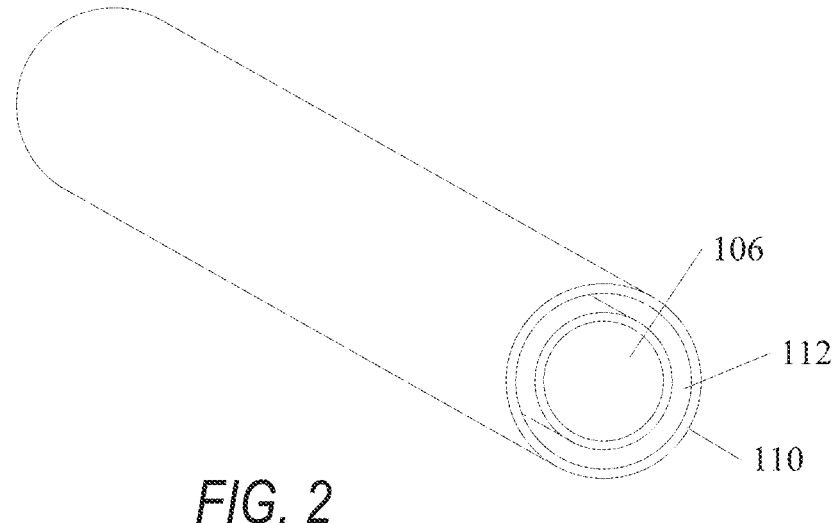
FIG. 2 shows an end view of a portion of a lithotriptor in accordance with some example embodiments.

FIG. 2 shows an assembly 200 that illustrates the distal end 106 of the hollow shaft 102 as inserted within a lumen 110. In the example shown in FIG. 2, a space 112 is provided between the hollow shaft 102 and the lumen 110. In one example, one or more lateral spacers are included to control dimensions of the space 112.

FIGS. 3-5 provide selected examples of lateral spacers. In FIG. 3, an assembly 300 is shown with a distal end 306 of a hollow shaft 302 similar to hollow shaft 102 from FIGS. 1 and 2. A spacer assembly 310 is shown extending from an outside surface 308 of the hollow shaft 302. In one example the spacer assembly 310 includes one or more fins 312 that form a finned cross section spacer assembly 310. In the example of FIG. 3, the one or more fins 312 are coupled to a hub 314 that fits over the outside surface 308 of the hollow shaft 302.

In one example, the spacer assembly 310 includes at least one longitudinal pathway through the spacer assembly 310. Arrow 320 shows a longitudinal pathway through the spacer assembly 310, while arrow 322 shows how fin 312 blocks longitudinal passage, or otherwise re-channels flow into a longitudinal pathway. As such, the fins 312 define one or more longitudinal pathways 320 through the spacer assembly 310. In one operation, as discussed in more detail below, liquid or other media is passed through the one or more longitudinal pathways 320 in the space (such as space 112 from FIG. 2) between the hollow shaft 302 and a lumen (such as lumen 110 from FIG. 2). The inclusion of spacer assembly 310 keeps the lumen 110 separated from the hollow shaft 302, while the longitudinal pathway 320 concurrently allows passage of liquid or media.

In the example shown, fins 312 are longitudinally aligned with an axis of the hollow shaft 302, although the invention is not so limited. In one example one or more of the fins 312 are angled to direct flow of the liquid or media. In select examples directing or concentrating flow with fins may improve flushing in an operation described in more detail in FIG. 6. In one example, angling fins 312 provides more consistent distributed support against the lumen 110 while minimizing any reduction in flow through the longitudinal pathways 320. In one example, only some of the fins 312 are angled. In one example, the fins 312 form a spiral finned cross section spacer.

FIG. 4 shows another assembly 400. The assembly 400 is shown with a distal end 406 of a hollow shaft 402 similar to hollow shaft 102 from FIGS. 1 and 2. A spacer assembly 410 is shown extending from an outside surface 408 of the hollow shaft 402. In one example the spacer assembly 410 includes an oval cross section spacer assembly 410 that includes a pair of opposed lobes 411. In other examples, one lobe 411 or more than two lobes 411 are included on a spacer assembly 410. In the example of FIG. 4, the spacer assembly 410 includes a center hole that fits over the outside surface 408 of the hollow shaft 402.

Similar to the example of FIG. 3, in one example, the spacer assembly 410 includes at least one longitudinal pathway through the spacer assembly 410. Arrow 420 shows a longitudinal pathway through the spacer assembly 410, while arrow 422 shows how lobe 411 blocks longitudinal passage, or otherwise re-channels flow into a longitudinal pathway. As such, the lobes 411 define one or more longitudinal pathways 420 through the spacer assembly 410. The inclusion of spacer assembly 410 keeps the lumen 110 separated from the hollow shaft 402, while the longitudinal pathway 420 concurrently allows passage of liquid or media.

FIG. 5 shows another assembly 500. The assembly 500 is shown with a distal end 506 of a hollow shaft 502 similar to hollow shaft 102 from FIGS. 1 and 2. A plurality of protrusions 510 are shown extending radially outward from an outside surface 508 of the hollow shaft 502. In one example the plurality of protrusions 510 include rounded bumps. Although rounded bumps are shown, the invention is not so limited. Other protrusion geometries include, but are not limited to, cylinders, ovals, rounded ovals, rectangles, squares, etc. In selected examples, rounded bumps minimizes contact area and friction with an inner surface of the lumen 110, while maintaining spacing such as space 112.

Similar to the examples of FIGS. 3 and 4, in one example, the plurality of protrusions 510 include at least one longitudinal pathway through the spacer assembly 510. Arrow 520 shows a longitudinal pathway through the spacer assembly 410, while arrow 522 shows how the plurality of protrusions 510 re-channel flow into a longitudinal pathway. As such, the plurality of protrusions 510 define one or more longitudinal pathways 520. The inclusion of the plurality of protrusions 510 keeps the lumen 110 separated from the hollow shaft 502, while the longitudinal pathway 520 concurrently allows passage of liquid or media. In one example the plurality of protrusions 510 allow for more open space along the outside surface 508 of the hollow shaft 502 to form larger, better flowing longitudinal pathways 520 compared to fins or lobes as described above.

In one example the plurality of protrusions 510 are adhered to the hollow shaft 502 with a separate adhesive layer. In one example the plurality of protrusions 510 are directly attached to the hollow shaft 502, for example deposited in a viscous state, and cooled on a surface of the hollow shaft 502.

In the example shown in FIG. 5, the plurality of protrusions 510 are adhered to the hollow shaft 502. In one example, the plurality of protrusions 510 are instead adhered to an inside surface of the lumen 110. Both configurations provide the space 112 shown in FIG. 2, as well as a longitudinal pathway. Likewise, other configurations of spacer assemblies described in the present disclosure may be coupled to an inside surface of the lumen 110 instead of an outside surface of the hollow shaft 502.

In examples described in the present disclosure, protrusions 510, fins 312, and lobes 411 are all examples of spacers. Although three examples of spacers are shown, the invention is not so limited. One of ordinary skill in the art, having the benefit of the present disclosure, will recognize that other shapes and sizes of spacers are also included.

The examples of FIGS. 3 and 4 illustrate singular examples of spacer assemblies. In other examples, the invention is not so limited. In selected examples, multiple spacer assemblies (i.e. 310, 410) are utilized on a single hollow shaft, and spaced apart along a length of the hollow shaft. By spacing out a number of spacer assemblies, a large unobstructed space between spacer assemblies will increase flow.

In examples with hubs, such as spacer assembly 310 and 410, the hubs may be adhered to the hollow shaft (302, 402) to fix them in place longitudinally along the hollow shaft (302, 402). In one example, an adhesive may be used. In one example, a mechanical interference fit may be used. In one example, the hubs of spacer assemblies 310 and 410 may be free sliding along a longitudinal axis of the hollow shaft (302, 402). The ability of the spacer assemblies 310 and 410 to move relative to the hollow shaft (302, 402) may reduce friction and/or wear. In one example, it is desirable to have spacer assemblies removable for cleaning/sterilization of reusable devices. In one example a stopper is included at a distal end of the hollow shaft (302, 402) to prevent one or more spacer assemblies from falling off the distal end. One example of a suitable stopper includes a polymer o-ring. In one example, multiple polymer o-rings may be used to hold free sliding spacer assemblies in place. The o-rings may later be removed in order to remove the spacer assemblies for cleaning/sterilization. In one example, the spacer assemblies are disposable, while the lithotriptor (hollow shaft, transducer, etc.) is reusable.

In one example all or a portion of a spacer assembly includes an elastomer material. In contrast to hard polymers, an elastomer provides a level of dampening of vibrations in a device system, such as a hollow shaft of a lithotriptor inside a lumen. In selected examples, a hard material may chatter or wear when cyclic motion is introduced, which may produce unwanted material shavings. In one example, by using an elastomer between a hollow shaft and a lumen as described, friction and/or wear is reduced or eliminated.

Any number of elastomer materials or combination of elastomer materials may be used. In one example, an elastomer material includes silicone. In one example, an elastomer material includes rubber. In one example, an elastomer material includes a polyether block amide. In one example, an elastomer material includes a polyurethane. In one example, an elastomer material includes a polyester. In one example the elastomer is biodegradable. A biodegradable elastomer provides an added level of safety in the event of any shavings coming off a spacer due to vibration.

Figure 6:
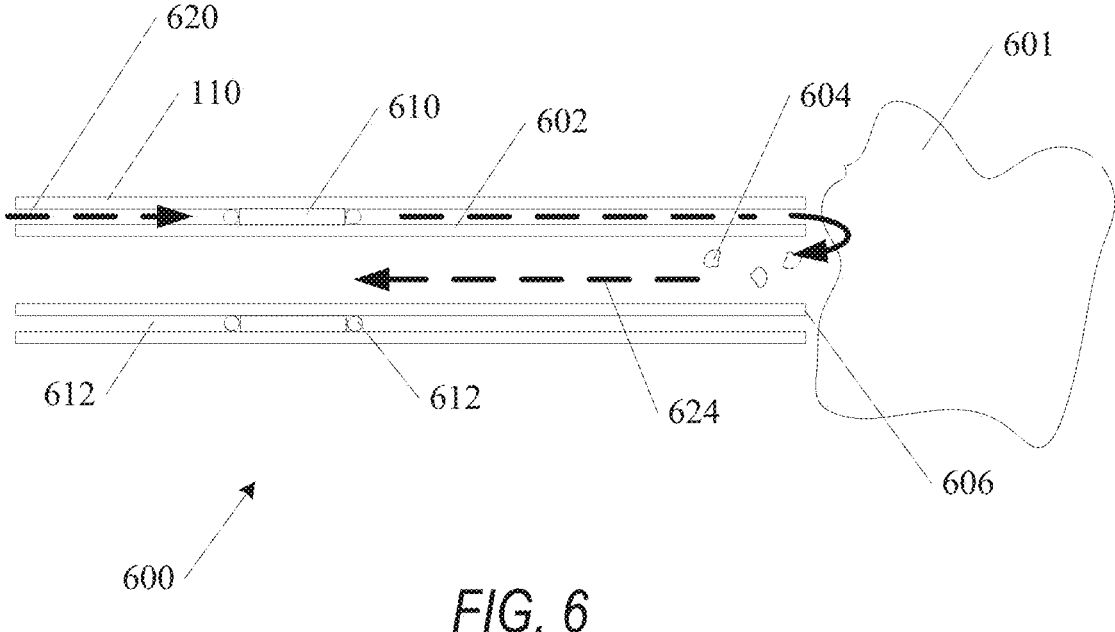
FIG. 6 shows a portion of a lithotriptor in operation in accordance with some example embodiments.

FIG. 6 shows one example of a procedure performed using devices and components described in examples above. A lithotriptor system 600 is shown, including a hollow shaft 602 and a lumen 110. A spacer assembly 610 is shown separating the hollow shaft 602 from the lumen 110, and providing a space 613. As described in examples above, in one example, spacer assembly 610 includes one or more longitudinal pathway through the spacer 610. In the example shown, one or more o-rings 612 may be included to hold the spacer assembly 610 in place along a longitudinal axis of the hollow shaft 602.

The hollow shaft 602 is shown with a distal end 606 adjacent to a stone 601 to be broken up and removed in small pieces 604. In operation, cyclic motion is generated in the hollow shaft 602, for example by a transducer in a handpiece as described above. The cyclic motion impacts the stone 601 and breaks off small pieces 604.

In one example, concurrently to the breaking operation, a media such as a liquid is passed through the space 612 along arrow 620. The media is allowed to pass each spacer assembly 610 through the longitudinal pathways as described in examples above. The media then flushes the small pieces 604 from the distal end 606 into an interior of the hollow shaft 602. The media and small pieces 604 are drawn along arrow 624 and are removed.

As discussed above, in one example, the spacer assembly 610 includes an elastomer material that provides a level of damping to one or more components in the lithotriptor system 600. The damping reduces or eliminates wear of components such as the hollow shaft 602 or the lumen 110.

FIG. 7 shows a flow diagram of an example method that may be performed using one or more of the devices described in the present disclosure. In operation 702, a hollow shaft is inserted into a lumen. A plurality of spacers are located between the hollow shaft and the lumen to define an infusion pathway between an outer surface of the hollow shaft and an inner surface of the lumen. In operation 704, cyclic motion is generated along the hollow shaft. In operation 706, a target object is broken up at a distal end of the hollow shaft with impacts from the cyclic motion. In operation 708, fluid is infused from a proximal end of the hollow shaft to a distal end of the hollow shaft through the infusion pathway and past the plurality of lateral spacers. In operation 710, at least some of the fluid and portions of the target object are removed through an interior of the hollow shaft.

To better illustrate the method and apparatuses disclosed herein, a non-limiting list of embodiments is provided here:

Example 1 includes a method of operating a lithotriptor. The method includes inserting a hollow shaft into a lumen, wherein a plurality of spacers are located between the hollow shaft and the lumen to define an infusion pathway between an outer surface of the hollow shaft and an inner surface of the lumen, generating cyclic motion along the hollow shaft, breaking a target object at a distal end of the hollow shaft with impacts from the cyclic motion, infusing fluid from a proximal end of the hollow shaft to a distal end of the hollow shaft through the infusion pathway and past the plurality of lateral spacers, and removing at least some of the fluid and portions of the target object through an interior of the hollow shaft.

Example 2 includes the method of example 1, wherein generating cyclic motion includes coupling a transducer to the hollow shaft to provide a wave signal.

Example 3 includes the method of any one of examples 1-2, wherein inserting the hollow shaft into the lumen includes inserting a hollow shaft into a lumen, wherein a plurality of elastomer spacers are located between the hollow shaft and the lumen with the plurality of elastomer spacers coupled to the hollow shaft.

Example 4 includes the method of any one of examples 1-3, further including damping at least a portion of the cyclic motion with the elastomer spacers.

Example 5 includes the method of any one of examples 1-4, wherein the plurality of lateral spacers includes a plurality of protruding bumps located between the hollow shaft and the lumen.

Example 6 includes the method of any one of examples 1-5, wherein the plurality of protruding bumps protrude from the outer surface of the hollow shaft.

Example 7 includes the method of any one of examples 1-6, wherein the plurality of protruding bumps protrude from the inner surface of the lumen.

Example 8 include a lithotriptor. The lithotriptor includes a transducer located in a handpiece, a hollow shaft extending from the handpiece and coupled to the transducer, an impact surface located at a distal end of the hollow shaft, one or more lateral elastomer spacers extending from an outside surface of the hollow shaft, and at least one longitudinal pathway through the one or more lateral spacers.

Example 9 includes the lithotriptor of example 8, wherein the one or more lateral elastomer spacers includes an oval cross section spacer.

Example 10 includes the lithotriptor of any one of examples 8-9, wherein the one or more lateral elastomer spacers includes a finned cross section spacer.

Example 11 includes the lithotriptor of any one of examples 8-10 wherein the finned cross section spacer includes a spiral finned cross section spacer.

Example 12 includes the lithotriptor of any one of examples 8-11, wherein the one or more lateral elastomer spacers are free sliding along a longitudinal axis of the hollow shaft.

Example 13 includes the lithotriptor of any one of examples 8-12, further including at least one o-ring retainer to hold at least one of the free sliding lateral elastomer spacers in place.

Example 14 includes the lithotriptor of any one of examples 8-13, wherein the one or more lateral elastomer spacers are fixed at a selected axial location along a longitudinal axis of the hollow shaft.

Example 15 includes the lithotriptor of any one of examples 8-14, wherein the one or more lateral elastomer spacers include silicone spacers.

Example 16 includes the lithotriptor of any one of examples 8-15, wherein the one or more lateral elastomer spacers include a biodegradable elastomer spacer.

Example 17 includes a lithotriptor. The lithotriptor includes a transducer located in a handpiece, a hollow shaft extending from the handpiece and coupled to the transducer, an impact surface located at a distal end of the hollow shaft, and a plurality of protrusions extending radially outward from an outside surface of the hollow shaft.

Example 18 includes the lithotriptor of example 17, wherein the plurality of protrusions includes elastomer protrusions.

Example 19 includes the lithotriptor of any one of examples 17-18, wherein the elastomer protrusions include silicone protrusions.

Example 20 includes the lithotriptor of any one of examples 17-19, wherein the plurality of protrusions includes rounded bumps.

Example 21 includes the lithotriptor of any one of examples 17-20, wherein the plurality of protrusions includes a biodegradable elastomer.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

The foregoing description, for the purpose of explanation, has been described with reference to specific example embodiments. However, the illustrative discussions above are not intended to be exhaustive or to limit the possible example embodiments to the precise forms disclosed. Many modifications and variations are possible in view of the above teachings. The example embodiments were chosen and described in order to best explain the principles involved and their practical applications, to thereby enable others skilled in the art to best utilize the various example embodiments with various modifications as are suited to the particular use contemplated.

It will also be understood that, although the terms "first," "second," and so forth may be used herein to describe various elements, these elements should not be limited by these terms. These terms are only used to distinguish one element from another. For example, a first contact could be termed a second contact, and, similarly, a second contact could be termed a first contact, without departing from the scope of the present example embodiments. The first contact and the second contact are both contacts, but they are not the same contact.

The terminology used in the description of the example embodiments herein is for the purpose of describing particular example embodiments only and is not intended to be limiting. As used in the description of the example embodiments and the appended examples, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The invention claimed is:

1. A lithotriptor, comprising:
a transducer located in a handpiece;
a hollow shaft extending from the handpiece and coupled to the transducer;
an impact surface located at a distal end of the hollow shaft;
one or more lateral elastomer spacers extending from an outside surface of the hollow shaft, wherein the one or more lateral elastomer spacers are free sliding along a longitudinal axis of the hollow shaft;
at least one longitudinal pathway through the one or more lateral elastomer spacers; and
at least one o-ring retainer abutting the one or more lateral elastomer spacers on one side, and exposed to the longitudinal pathway on a second side of the o-ring opposite the one or more lateral elastomer spacers to hold at least one of the lateral elastomer spacers in place.

2. The lithotriptor of claim 1, wherein the one or more lateral elastomer spacers includes an oval cross section spacer.

3. The lithotriptor of claim 1, wherein the one or more lateral elastomer spacers includes a finned cross section spacer.

4. The lithotriptor of claim 3, wherein the finned cross section spacer includes a spiral finned cross section spacer.

5. The lithotriptor of claim 1, wherein the one or more lateral elastomer spacers are fixed at a selected axial location along a longitudinal axis of the hollow shaft.

6. The lithotriptor of claim 1, wherein the one or more lateral elastomer spacers include silicone spacers.

7. The lithotriptor of claim 1, wherein the one or more lateral elastomer spacers include a biodegradable elastomer spacer.

* * * * *